(12) United States Patent
Malpart et al.

(10) Patent No.: US 11,713,296 B2
(45) Date of Patent: Aug. 1, 2023

(54) SALTS OF METHYL 6-(2,4-DICHLORO-PHENYL)-5-[4-[(3S)-L-(3-FLUOROPROPYL) PYRROLIDIN-3-YL]OXYPHENYL]-8,9-DIHYDRO-7H-BENZO[7]ANNULENE-2-CARBOXYLATE AND PREPARATION PROCESS THEREOF

(71) Applicant: Sanofi, Paris (FR)

(72) Inventors: Joël Malpart, Paris (FR); José Ruiz Montes, Paris (FR)

(73) Assignee: SANOFI, Paris (FR)

( * ) Notice: Subject to any disclaimer, the term of this patent is extended or adjusted under 35 U.S.C. 154(b) by 0 days.

(21) Appl. No.: 17/193,776

(22) Filed: Mar. 5, 2021

(65) Prior Publication Data

US 2021/0188772 A1     Jun. 24, 2021

Related U.S. Application Data

(63) Continuation of application No. PCT/EP2019/073823, filed on Sep. 6, 2019.

(30) Foreign Application Priority Data

Sep. 7, 2018  (EP) ..................................... 18306177

(51) Int. Cl.
| C07D 207/12 | (2006.01) |
| B01J 31/16  | (2006.01) |
| C07C 55/07  | (2006.01) |
| C07C 59/255 | (2006.01) |

(52) U.S. Cl.
CPC ........ *C07D 207/12* (2013.01); *B01J 31/1616* (2013.01); *C07C 55/07* (2013.01); *C07C 59/255* (2013.01)

(58) Field of Classification Search
CPC .... C07D 207/12; B01J 31/1616; C07C 55/07; C07C 59/255; A61K 31/4015
See application file for complete search history.

(56) References Cited

U.S. PATENT DOCUMENTS

| 6,495,607 B2 | 12/2002 | Bohlmann et al. |
| 7,429,681 B2 | 9/2008  | Pinney et al.   |
| 7,612,114 B2 | 11/2009 | Hamaoka et al.  |
| 7,799,824 B2 | 9/2010  | Lagu et al.     |
| 8,299,112 B2 | 10/2012 | Smith et al.    |
| 9,309,211 B2 | 4/2016  | Xiao et al.     |
| 9,540,361 B2 | 1/2017  | Djicks et al.   |

(Continued)

FOREIGN PATENT DOCUMENTS

| CN | 1309635     | 8/2001 |
| CN | 106924210 A | 7/2017 |

(Continued)

OTHER PUBLICATIONS

Anstead, Gregory M. et al., "2,3-Diarylindenes and 2,3-Diarylindenones: Synthesis, Molecular Structure, Photochemistry, Estrogen Receptor Binding Activity, and Comparisons with Related Triarylethylenes", J. Med.Chem., 1988, vol. 31, No. 7, pp. 1316-1326.

(Continued)

*Primary Examiner* — Brandon J Fetterolf
*Assistant Examiner* — Lauren Wells
(74) *Attorney, Agent, or Firm* — McNeill Baur PLLC

(57) ABSTRACT

Herein are provided novel salts of methyl 6-(2,4-dichlorophenyl)-5-[4-[(3S)-1-(3-fluoropropyl)pyrrolidin-3-yl]oxyphenyl]-8,9-dihydro-7H-benzo[7]annulene-2-carboxylate namely the oxalate salt and the dibenzoyltartrate salt

2 Claims, No Drawings

(56) References Cited

U.S. PATENT DOCUMENTS

| | | |
|---|---|---|
| 9,714,221 B1 | 7/2017 | Bouaboula et al. |
| 9,845,291 B2 | 12/2017 | Liang et al. |
| 10,570,090 B2 | 2/2020 | Bouaboula et al. |
| 10,966,963 B2 | 4/2021 | Labadie et al. |
| 11,149,031 B2 | 10/2021 | Bouaboula et al. |
| 11,214,541 B2 | 1/2022 | Bouaboula et al. |
| 11,260,057 B2 | 3/2022 | Bouaboula et al. |
| 2012/0130219 A1 | 5/2012 | Zhao et al. |
| 2013/0252890 A1 | 9/2013 | Wintermantel et al. |
| 2015/0080438 A1 | 3/2015 | Wintermantel et al. |
| 2015/0157606 A1 | 6/2015 | Chow Maneval et al. |
| 2016/0184311 A1 | 6/2016 | Chen et al. |
| 2018/0153828 A1 | 6/2018 | Garner et al. |
| 2020/0155521 A1 | 5/2020 | Schwartz et al. |
| 2020/0352905 A1 | 11/2020 | Cartot-Cotton et al. |
| 2020/0361918 A1 | 11/2020 | Bouaboula et al. |
| 2020/0392081 A1 | 12/2020 | Bouaboula et al. |
| 2021/0188771 A1 | 6/2021 | Rabion et al. |
| 2022/0073460 A1 | 3/2022 | Bouaboula et al. |
| 2022/0362248 A1 | 11/2022 | Pouaboula et al. |

FOREIGN PATENT DOCUMENTS

| | | |
|---|---|---|
| EP | 1229036 A1 | 8/2002 |
| EP | 3434272 A1 | 1/2019 |
| JP | 2002520388 A | 7/2002 |
| JP | 2005528320 A | 9/2005 |
| JP | 2008512348 A | 4/2008 |
| JP | 2008546706 A | 12/2008 |
| JP | 2011500538 A | 1/2011 |
| JP | 2015500814 A | 1/2015 |
| WO | 1992015579 A1 | 9/1992 |
| WO | 2000003979 A1 | 1/2000 |
| WO | 2003016270 A2 | 2/2003 |
| WO | 2003091239 A1 | 11/2003 |
| WO | 2004058682 A1 | 7/2004 |
| WO | 2006012135 A1 | 2/2006 |
| WO | 2006138427 A2 | 12/2006 |
| WO | 2009047343 A1 | 4/2009 |
| WO | 2009101634 A2 | 8/2009 |
| WO | 2012037410 A2 | 3/2012 |
| WO | 2012037411 A2 | 3/2012 |
| WO | 2012068284 A2 | 5/2012 |
| WO | 2013097773 A1 | 7/2013 |
| WO | 2015028409 A1 | 3/2015 |
| WO | 2016097071 A1 | 6/2016 |
| WO | 2016097072 A1 | 6/2016 |
| WO | 2016176666 A1 | 11/2016 |
| WO | 2017/140669 A1 | 8/2017 |
| WO | 2018/091153 A1 | 5/2018 |
| WO | 2019020559 A1 | 1/2019 |

OTHER PUBLICATIONS

McCague, Raymond et al., "Nonisomerizable Analogues of (Z)- and (E)-4-Hydroxytamoxifen. Synthesis and Endocrinological Properties of Substituted Diphenylbenzocycloheptenes", J. Med.Chem., 1988, vol. 31, No. 7, pp. 1285-1290.

International Search Report for PCT/EP2019/073823, dated Oct. 10, 2019, 3 pages.

International Search Report for PCT/EP2019/073827, dated Oct. 9, 2019, 3 pages.

Deroo, B.J., et al., "Estrogen Receptors and Human Disease", The Journal of Clinical Investigation, Mar. 2006, vol. 116, No. 3, pp. 561-570.

Golub et al., "Molecular Classification of Cancer: Class Discovery and Class Prediction by Gene Expression Monitoring", Science, Oct. 15, 1999, vol. 286, pp. 531-537.

International Search Report for International Application No. PCT/EP2017/053282, dated Jul. 6, 2017.

International Search Report for International Application No. PCT/EP2017/068446, dated Sep. 12, 2017.

International Search Report for International Application No. PCT/EP2018/069901, dated Oct. 12, 2018.

Lala, P.K., et al., "Role of Nitric Oxide in Tumor Progression: Lessons From Experimental Tumors", Cancer Metastasis Reviews, Mar. 1998, vol. 17, No. 1, pp. 91-106.

Pending U.S. Appl. No. 16/414,558, filed May 16, 2019.

Pending U.S. Appl. No. 16/634,089, filed Jan. 24, 2020.

Pending U.S. Appl. No. 17/124,852, filed Dec. 17, 2020.

Ruff, et al., "Estrogen Receptor Transcription and Transactivation Structure-Function Relationship in DNA- and Ligand-Binding Domains of Estrogen Receptors", Breast Cancer Research, 2000, vol. 2, No. 5, pp. 353-359.

Translation of Office Action issued in Japanese Application No. 2018-515615, dated Sep. 18, 2018, 3 pages.

Translation of Search Report issued in Chinese Application No. 201780023008.0, dated Apr. 23, 2020, 3 pages.

Franks, et al., "Selective Estrogen Receptor Modulators: Cannabinoid Receptor Inverse Agonists with Differential CB1 and CB2 Selectively," Frontiers in Pharmacology, 7(503): 1-16 (2016).

Jordan, Craig V., "Antiestrogens and Selective Estrogen Receptor Modulators as Multifunctional Medicines. 1. Receptor Interactions," Journal of Clinical Chemistry, 46(6): 883-908 (2003).

Miller, Chris P., "SERMs: Evolutionary Chemistry, Revolutionary Biology," Current Pharmaceutical Design, 8(23):2089-2111 (2002).

Pickar, et al., "SERMs: Progress and future perspectives," Maturitas, Elsevier, 67:129-138 (2010).

Ullrich, et al., "Estrogen receptor modulator review," Expert Opinion, 16(5):559-572.

Bardia, A., et al., Dose-escalation study of SAR439859, an oral selective estrogen receptor (ER) degrader (SERD), in postmenopausal women with ER+/HER2- metastatic breast cancer (mBC), Journal of Clinical Oncology, vol. 37, Suppl. 15, p. 1054 (May 20, 2019).

Campone, M., et al., "Abstract P5-11-02: Dose-escalation study of SAR439859, an oral selective estrogen receptor degrader, in postmenopausal women with estrogen receptor-positive and human epidermal growth factor receptor 2-negative metastatic breast cancer," Cancer Research, vol. 80, Suppl. 4, pp. 1-4 (Feb. 2020).

Extended European Search Report issued in European Application No. 19305593.6 dated Oct. 30, 2019, 7 pages.

International Search Report for PCT/EP2020/062743, dated Aug. 10, 2020.

Sylvaine Cartot-Cotton et al., Pending U.S. Appl. No. 16/870,031, filed May 8, 2020.

Monsif Bouaboula et al., Pending U.S. Appl. No. 17/460,629, filed Aug. 30, 2021.

Monsif Bouaboula et al., Pending U.S. Appl. No. 17/532,051, filed Nov. 22, 2021.

Boinsard, S., et al., Pending U.S. Appl. No. 17/765,169, filed Mar. 30, 2022.

Bouaboula, M., et al., Pending U.S. Appl. No. 17/802,223, filed Aug. 25, 2022.

Ei-Ahmad, Y., et al., "Discovery of 6-(2,4-Dichlorophenyl)-5-[4-[(3S)-1-(3-fluoropropyl)-pyrrolidin-3-yl]-oxyphenyl]-8,9-dihydro-7H-benzo[7]annulene-2-carboxylic acid (SAR439859), a Potent and Selective Estrogen Receptor Degrader (SERD) for the Treatment of Estrogen-Receptor-Positive Breast Cancer," Journal of Medicinal Chemistry, vol. 63, No. 2, pp. 512-528 (2019).

Gould, P., "Salt selection for basic drugs," International Journal of Pharmaceutics, vol. 33, pp. 201-217 (1986).

International Search Report for PCT/EP2020/085011, dated Jan. 25, 2021.

International Search Report for PCT/EP2021/054815, dated May 12, 2021.

Jordan, Craig V., "Antiestrogens and Selective Estrogen Receptor Modulators as Multifunctional Medinies. 1. Receptor Interactions," ournal of Medicinal Chemistry, 46(6): 883-908 (2003).

Mannava, M.K.C., et al., "Enhanced Bioavailability in the Oxalate Salt of the Antituberculosis Drug Ethionamide," Crystal Growth & Design, vol. 16(3), pp. 1591-1598, (2016).

Rabion, A et al., Pending U.S. Appl. No. 17/193,706, filed Mar. 5, 2021.

RN 1861739-57-2, Registry Database Compound, 2016.

(56) References Cited

OTHER PUBLICATIONS

Billot P., et al., Pending U.S. Appl. No. 17/783,364, filed Jun. 8, 2022.
Bouaboula, M., et al.. Pending U.S. Appl. No. 17/579,187, filed Jan. 19, 2022. (available on IFW).

SALTS OF METHYL 6-(2,4-DICHLORO-PHENYL)-5-[4-[(3S)-L-(3-FLUOROPROPYL) PYRROLIDIN-3-YL]OXYPHENYL]-8,9-DIHY-DRO-7H-BENZO[7]ANNULENE-2-CARBOXY-LATE AND PREPARATION PROCESS THEREOF

The present application is a continuation of International Application No. PCT/EP2019/073823, filed Sep. 6, 2019, which claims priority from European Patent Application No. 18306177.9, filed Sep. 7, 2018, each of which is incorporated by reference herein in its entirety for any purpose.

Herein are provided novel salts of methyl 6-(2,4-dichlorophenyl)-5-[4-[(3S)-1-(3-fluoropropyl)pyrrolidin-3-yl]oxyphenyl]-8,9-dihydro-7H-benzo[7]annulene-2-carboxylate.

Methyl 6-(2,4-dichlorophenyl)-5-[4-[(3S)-1-(3-fluoropropyl)pyrrolidin-3-yl]oxyphenyl]-8,9-dihydro-7H-benzo[7]annulene-2-carboxylate, also named as 6-(2,4-dichlorophenyl)-5-[4-[(3S)-1-(3-fluoropropyl)pyrrolidin-3-yl]oxyphenyl]-8,9-dihydro-7H-benzo[7]annulene-2-carboxylic acid methyl ester and hereafter designated as "compound (2)", is the N-1 intermediate in the synthesis of 6-(2,4-dichlorophenyl)-5-[4-[(3S)-1-(3-fluoropropyl)pyrrolidin-3-yl]oxyphenyl]-8,9-dihydro-7H-benzo[7]annulene-2-carboxylic acid (hereafter "compound (1)"). Indeed, compound (1) can be obtained by saponification of compound (2).

Compound (1), depicted below, is a selective estrogen receptor degrader (SERD) which has estrogen receptor antagonist properties and accelerates the proteasomal degradation of the estrogen receptor. It may be used in particular as anticancer agent. This compound is disclosed in the patent application WO 2017/140669.

(1)

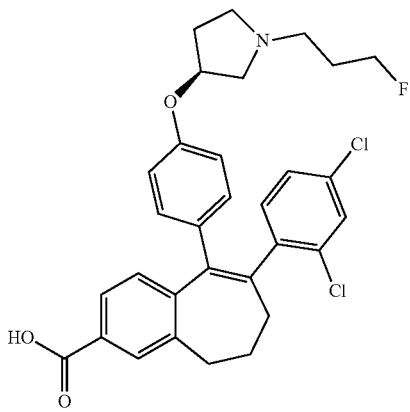

For active ingredients in medicinal products and their synthesis intermediates there is always a need to find new synthesis routes more adapted for industrial implementation.

Herein are provided novel salt forms of compounds (2), namely an oxalate salt of said compound:

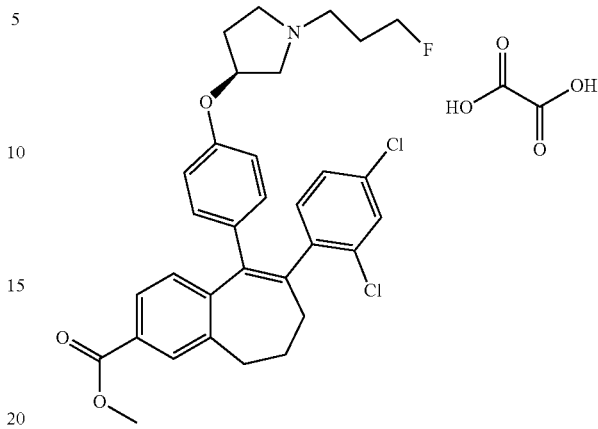

and a dibenzoyltartrate salt:

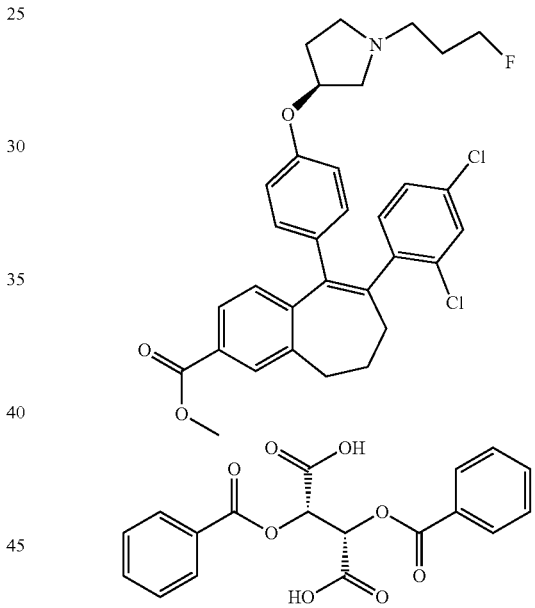

Herein are further provided processes for the preparation of the above-mentioned salt forms of compounds (2), namely:

a process for the preparation of an oxalate salt of compound (2), comprising the step of adding oxalic acid to said compound (2) in a solvent chosen from ester-type solvent, ether-type solvent and toluene; and a process for the preparation of a dibenzoyltartrate salt of compound (2), comprising the step of adding dibenzoyl tartaric acid to said compound in a mixture of toluene and heptane.

Said salts according to the present invention are particularly useful in the framework of the preparation of compound (1) as defined above. The advantages of said salts will be apparent from the detailed description of said process.

The salts according to the invention may be obtained according to the preparation processes detailed herein after.

WO 2017/140669 Route

In particular, the salts according to the invention may be obtained following the route of synthesis as described in the patent application WO 2017/140669 as represented in Scheme 3 and 4 herein after. The step before obtaining the salt is represented by the scheme below.

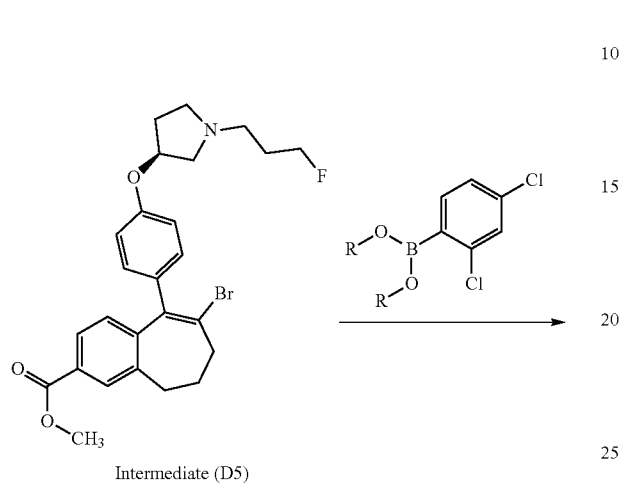

Intermediate (D5)

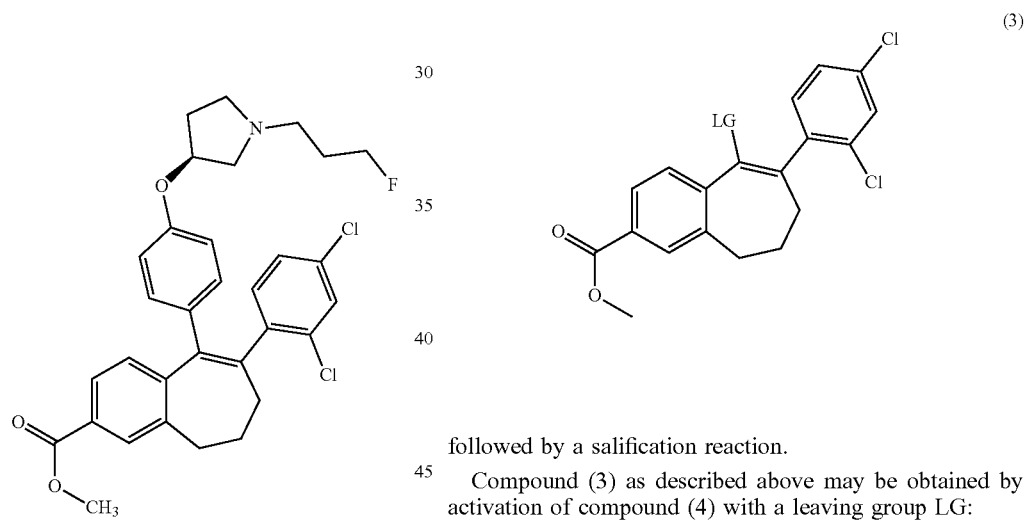

Compound (2)

Said step may be followed by a salification step as detailed herein after.

Example 5 of the present application starts from intermediate (D5) for forming via a Suzuki coupling a compound (2) as defined herein above, which is itself used for forming a salt of compound (2).

Alternatively, the salts according to the invention may be obtained by a salification step following a Suzuki coupling in the framework of the preparation of compound (2) as an improved process which is detailed hereinafter.

Improved Process

The present text describes a process for the preparation of compound (2) (methyl ester of compound (1)) implementing the salt forms described above:

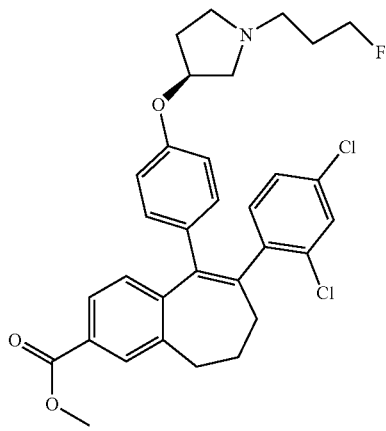

in salts forms, characterized in that compound (2) may be obtained by a Suzuki coupling of compound (3), wherein LG represents a leaving group, with an organoboron reagent:

followed by a salification reaction.

Compound (3) as described above may be obtained by activation of compound (4) with a leaving group LG:

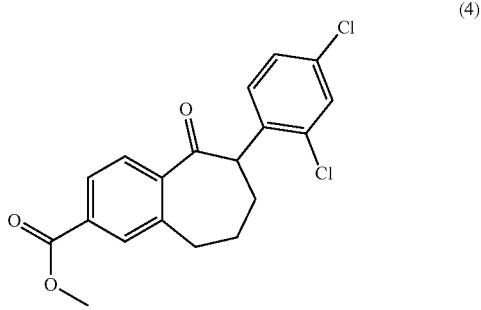 [SMILES: COC(=O)c1ccc2c(c1)CCCC(c1ccc(Cl)cc1Cl)C2=O]

Compound (4) as described above may be obtained by alpha-arylation of methyl 5-oxo-6,7,8,9-tetrahydro-5H-benzo[7]annulene-2-carboxylate (represented as compound (5) below) with 1-LG'-2,4-dichlorobenzene as defined herein after:

LG' represents any leaving group.

LG' may represents i. a leaving group of the formula —O—SO$_2$—C$_n$F$_{(2n+1)}$ with n=1 to 4, more particularly a triflate (wherein n=1) or a nonaflate (wherein n=4), or ii. a halogen atom selected from bromine or iodine.

1-LG'-2,4-dichlorobenzene may be 1-Hal-2,4-dichlorobenzene, wherein Hal represents a halogen atom selected from bromine or iodine:

The leaving groups LG and LG' are defined as a chemical moiety displaying leaving group properties and allowing further substitution in a subsequent chemical reaction.

More particularly, the leaving group LG in compound (3) may be obtained by activating the carbonyl function in compound (4). Conventional activation reactions of the carbonyl function in compound (4) may be used as known to one of skill in the Art.

For example, the leaving group LG in compound (3) may be a halogen atom or an alkyl or aryl sulfamate, an alkyl or aryl phosphate or an alkyl or aryl sulfonate, in particular a halogen atom or an alkyl or aryl sulfonate.

The leaving group LG may be a halogen atom or a mesylate, tosylate, sulfamate, phosphate, triflate or nonaflate group.

The leaving group in compound (3) may be a halogen atom or a mesylate, tosylate, sulfamate, phosphate or triflate group.

The leaving group LG may be a triflate or a nonaflate group.

Advantageously, the leaving group LG is the triflate group (trifluoromethanesulfonyl, corresponding to the formula —O—S(O)$_2$—CF$_3$).

In the context of the present specification, the terms below have the following definitions unless otherwise mentioned throughout the instant specification:

- an alkyl group: a linear or branched saturated hydrocarbon-based aliphatic group comprising, unless otherwise mentioned, from 1 to 6 carbon atoms (noted "(C$_1$-C$_6$)-alkyl"). By way of examples, mention may be made of, but not limited to: methyl, ethyl, propyl, n-propyl, isopropyl, butyl, isobutyl, sec-butyl, tert-butyl, pentyl, isopentyl, hexyl and isohexyl groups, and the like. Said groups may be partially or fully substituted by fluorine atoms and include but not be limited to perfluoromethyl, perfluoroethyl, perfluoropropyl, perfluorobutyl, and the like;
- an aryl group: phenyl, naphtyl or substituted phenyl, wherein a substituted phenyl is defined as a phenyl group in which one or more of the hydrogens has been replaced by the same or different substituents including, but not limited to: halogen atom, alkyl, nitro, cyano, alkoxy, aryl, heteroaryl and trifluoromethyl groups, and the like.

Compound (4) may be activated into compound (3'), wherein compound (3') is defined as compound (3) wherein LG represents the triflate group. The activation of compound (4) into compound (3') is a triflation reaction:

In such a reaction a triflation reagent is used, such as N-phenylbistriflimide or triflic anhydride.

Advantageously, N-phenylbistriflimide, also known as N,N-bis(trifluoromethylsulfonyl)aniline, is used as the triflation reagent. This reagent is advantageously used in a slight excess amount relative to compound (4), such as about 1.3 eq. (equivalent).

Suitable triflation media depend on the triflation reagent used, as known to one of skill in the Art.

The triflation reaction is carried out is an appropriate organic solvent, for example THF (tetrahydrofuran), Me-THF (methyl-tetrahydrofuran), acetonitrile, dioxane, or a mixture of toluene with Me-THF. Advantageously, Me-THF is used as organic solvent.

The triflation reaction is advantageously carried out with N-phenylbistriflimide as triflation reagent, in Me-THF as organic solvent. The temperature for the triflation reaction is advantageously chosen between 0° C. and room temperature.

The triflation reaction is carried out with a strong base, for example sodium hydride (NaH), potassium bis(trimethylsilyl)amide (KHMDS) or a phosphazene base such as BEMP (2-tert-butylimino-2-diethylamino-1,3-dimethylperhydro-1,3,2-diazaphosphorine) or BTPP (tert-butylimino-tri(pyrrolidino)phosphorane). Advantageously, sodium hydride is used as a strong base.

When NaH is used as strong base, the triflation reaction is carried out with a catalyst, for example DBU (1,8-diazabicyclo[5.4.0]undec-7-ene) or DBN (1,5-diazabicyclo(4.3.0)non-5-ene). Advantageously, DBU is used as catalyst.

Advantageously, the triflation reaction is carried out with sodium hydride as strong base, and with DBU as catalyst. Advantageously, a catalytic amount of DBU is used in the triflation reaction (such as about 0.2 eq.) and a stoichiometric amount of NaH (such as about 1.0-1.1 eq.), or a sub-stoichiometric amount of NaH (about 0.7-0.8 eq.) and a stoichiometric amount of DBU (about 1.0-1.2 eq.).

The triflation reaction is advantageously followed by a crystallization of the product obtained, according to crystallization techniques known to one of skill, so as to obtain compound (3) in a high purity, such as a purity level equal to or greater than 99%, before having it undergo the next steps of the process. Such a crystallization step may be carried out for example in acetonitrile, tert-amyl alcohol, heptane or diisopropylether. Advantageously, the crystallization is carried out in acetonitrile. The crystallization in acetonitrile is advantageously carried out at 0° C. and may be followed by drying at about 45° C.

The alpha-arylation of compound (5) to produce compound (4) may be carried out with 1-iodo-2,4-dichlorobenzene or with 1-bromo-2,4-dichlorobenzene, which are both commercially available reactants. Advantageously, 1-bromo-2,4-dichlorobenzene is used as alpha-arylation reactant.

This alpha-arylation step may be carried out in an organic solvent, in presence of a palladium derivative as catalyst, of an appropriate ligand for the alpha-arylation reaction, and of a mineral base.

Advantageously, the alpha-arylation step may be carried out in xylene, toluene, butyl acetate, isopropyl acetate or THF as organic solvent, using palladium(II) acetate (Pd(OAc)$_2$) or tris(dibenzylideneacetone)dipalladium(0) (Pd$_2$dba$_3$) as catalyst, and Xantphos (4,5-bis(diphenylphosphino)-9,9-dimethylxanthene) as ligand. Alternatively, when Pd$_2$dba$_3$ is used as catalyst, DPEPhos (bis[(2-diphenylphosphino)phenyl]ether) may be used as ligand. Another possible palladium derivative for use in the alpha-arylation step is [1,1'-bis(di-tert-butylphosphino)ferrocene]dichloropalladium(II) (PdCl$_2$(dtbpf)). Advantageously, the alpha-arylation step may be carried out in toluene as organic solvent and with Pd$_2$dba$_3$ as catalyst. Under these conditions, heating at reflux may be applied.

Advantageously, the alpha-arylation step may be carried out in the presence of a mineral base, such as K$_2$CO$_3$, K$_3$PO$_4$, Cs$_2$CO$_3$ and tBuONa. The mineral base is advantageously present in excess, such as 1.5 to 4 equivalent (eq.), more particularly 2.5 to 4 eq., in respect to the compound (5).

The Suzuki reaction applied on compound (3) to produce compound (2) may be defined as a coupling reaction using an organoboron reagent and a transition metal-based catalyst, advantageously a palladium-based catalyst.

Advantageously, the organoboron reagent for use in the Suzuki coupling step of the process described herein may be reagent (1), namely (3S)-1-(3-fluoropropyl)-3-[4-(4,4,5,5-tetramethyl-1,3,2-dioxaborolan-2-yl)phenoxy]pyrrolidine, which is described in the patent application WO 2017/140669, or the corresponding acid (named reagent (2) as illustrated below), obtained by hydrolysis of the ester moiety of reagent (1), or a salt thereof such as the trifluoroborate potassium salt (named reagent (3) as illustrated below), obtained by salification of the boronic acid or ester moiety of reagent (2) or (1) by potassium hydrogen difluoride (KHF$_2$):

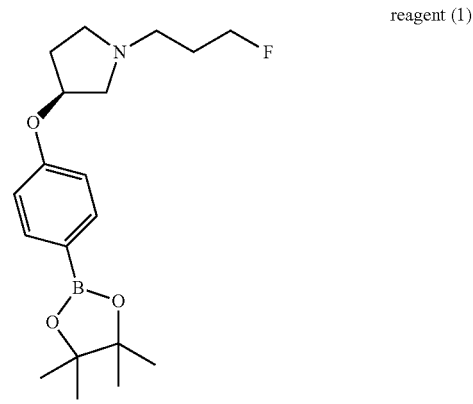

reagent (1)

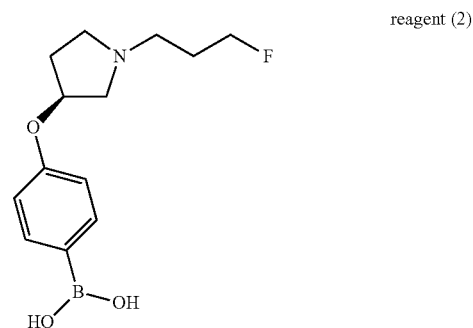

reagent (2)

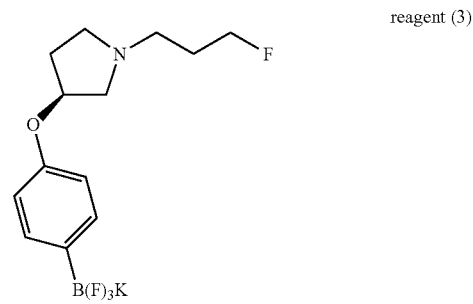

reagent (3)

The content of patent application WO 2017/140669 for the preparation of (3S)-1-(3-fluoropropyl)-3-[4-(4,4,5,5-tetramethyl-1,3,2-dioxaborolan-2-yl)phenoxy]pyrrolidine (reagent (1)) is herein incorporated by reference.

The organoboron reagent for use in the Suzuki coupling step of the process described herein may advantageously be used in an equimolar amount (i.e. about 1 eq.) relative to the compound (3).

The palladium-based catalyst for use in the Suzuki coupling step of the process described herein may advantageously be the palladium complex bis(triphenylphosphine) palladium(II) dichloride, of formula $PdCl_2(PPh_3)_2$.

It is used in catalytic amount, for example at an amount of about 0.05 eq.

Suitable reaction media for the Suzuki coupling step of the process described herein depend on the specific reagents used, as known to one of skill in the Art.

When bis(triphenylphosphine)palladium(II) dichloride is used as a catalyst, the reaction may advantageously be carried out with an inorganic base, such as cesium carbonate ($Cs_2CO_3$), and in an organic solvent, such as a water/acetonitrile ($CH_3CN$) mixture.

Salification Step

The salification step as described herein after can be implemented for both routes of synthesis (WO 2017/140669 route and the improved route).

Both routes contain a Suzuki coupling step before such salification step.

Still in the framework of the preparation of compound (2), a salification reaction may be performed after the Suzuki coupling step so as to obtain compound (2) in a salt form according to the present invention, advantageously in the form of an oxalate salt or of a dibenzoyltartrate salt.

The Suzuki coupling may thus be followed by a salification reaction, for example for obtaining an oxalate salt of compound (2) or a dibenzoyltartrate salt of compound (2).

The oxalate salt of compound (2) provided herein may be obtained using oxalic acid in a solvent selected from an ester-type solvent, such as an acetate solvent (for example ethyl acetate or isopropyl acetate), an ether-type solvent, such as MTBE (methyl-tertbutyl ether) or diisopropyl ether, and toluene.

Advantageously, the oxalate salt of compound (2) may be obtained using oxalic acid in isopropylacetate, under heating, for example between 60° C. and 80° C., preferably at about 70° C.

The said process forms part of the present invention.

Thus, the present invention further provides a process for the preparation of an oxalate salt of compound (2), comprising the step of adding oxalic acid to a compound (2) in a solvent chosen from ester-type solvent, ether-type solvent and toluene.

In a particular embodiment, the ester-type solvent is an acetate solvent, in particular ethyl acetate or isopropyl acetate, more particularly isopropyl acetate.

In another embodiment, the ether-type solvent is chosen from methyl-tertbutyl and diisopropyl ether.

In a particular embodiment, the process for the preparation of an oxalate salt of compound (2) is carried out in isopropyl acetate, under heating, in particular between 60° C. and 80° C. and more particularly at 70° C.

The dibenzoyltartrate salt of compound (2) provided herein may be obtained using dibenzoyl tartaric acid (also named (2R,3R)-2,3-dibenzoyloxybutanedioic acid), in a mixture of toluene and heptane.

The said process forms part of the present invention.

Thus, the present invention further provides a process for the preparation of a dibenzoyltartrate salt of compound (2), comprising the step of adding dibenzoyl tartaric acid to a compound (2) in a mixture of toluene and heptane.

The term "salification" of compound (2) as described above refers to the formation of a salt, allowing to precipitate compound (2).

Especially for the oxalate salt, such salification step allows to recover compound (2) from the reaction mixture in high purity. It also allows avoiding the use of a column chromatography for recovering the compound (2) from the reaction mixture in high purity.

Such a route of synthesis with a salt formation is particularly convenient for the industrial scale and for the storage of compound (2).

Example 6 of the present application illustrates the suitable solvents for various ways of obtaining the claimed salts.

The dibenzoyl tartrate salt of compound (2) precipitates with a purity of about 93%, and the oxalate salt of compound (2) with a purity level equal to or greater than 98%.

In view of the above description, the process described herein for the preparation of compound (2) is represented in scheme 1 below, wherein LG' and LG are as defined above:

Scheme 1

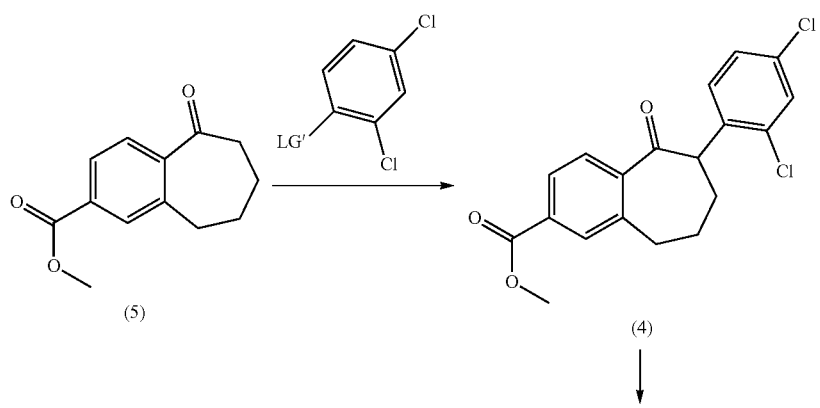

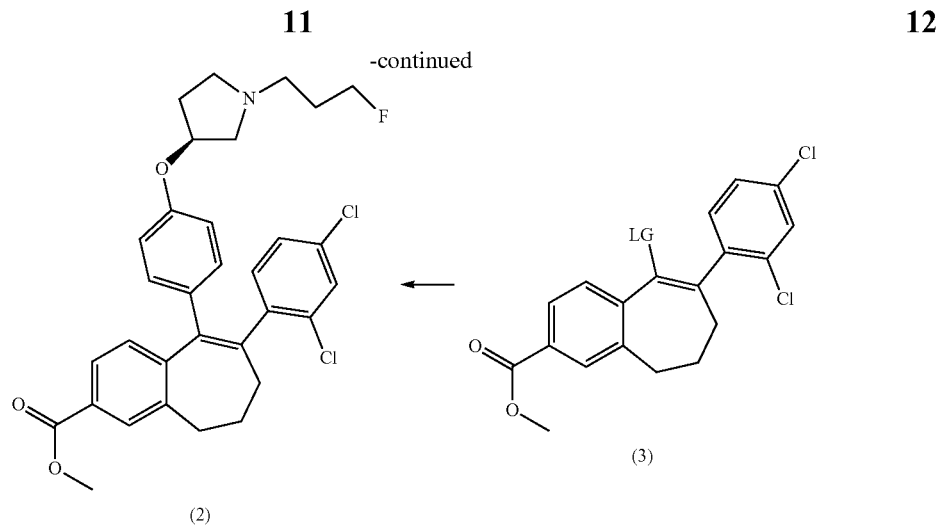

The process described herein for the preparation of compound (2) is also represented in scheme 2 below, wherein LG' is as defined above:

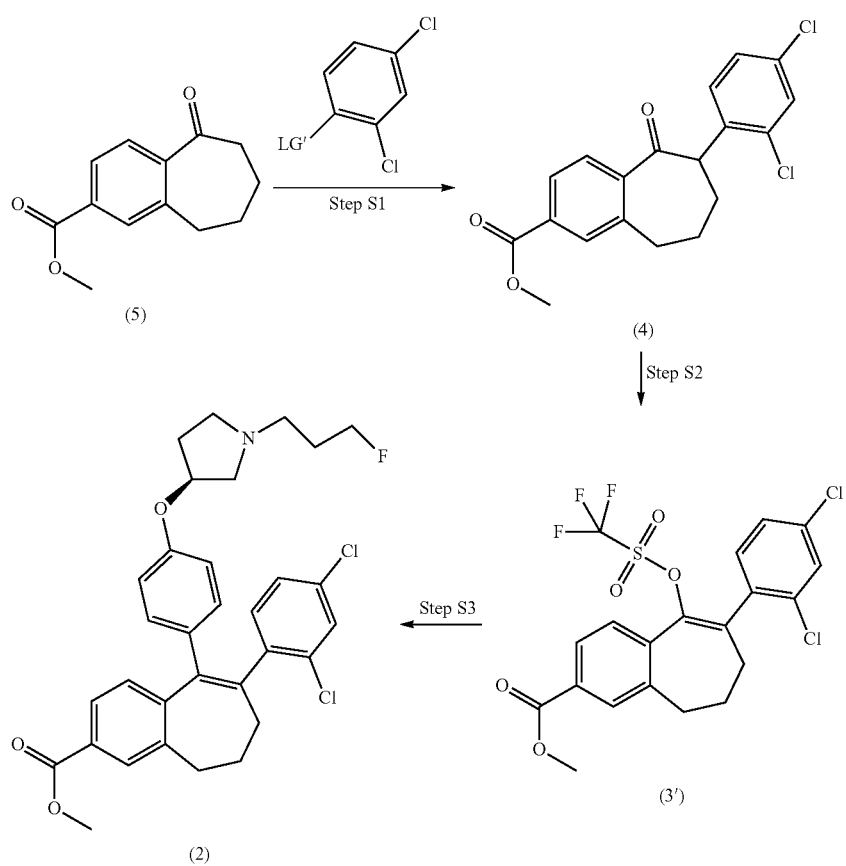

Compound (2) may undergo a saponification reaction, whereby the hydrolysis of the ester function will yield compound (1), bearing the corresponding acidic function. Such a saponification reaction may be carried out under conditions known to one of skill in the Art, namely in basic medium, advantageously using sodium hydroxide as a base, and in an organic solvent, advantageously an alcoholic solvent, such as methanol. Heating is applied during the saponification reaction so as to accelerate the hydrolysis of the ester moiety, for example at about 60° C. Such a saponification reaction is described in the patent application WO 2017/140669.

As a salt form of compound (2) is used, a free base of compound (2) is prepared before carrying out the saponification reaction, for example using an aqueous solution of potassium carbonate.

Described herein is also a process for the preparation of compound (1):

(1)

by saponification of compound (2):

(2)

wherein compound (2) is obtained by the process described above.

Disclosed herein are also compounds (4), (3) and (3'), wherein LG represents a leaving group as described above:

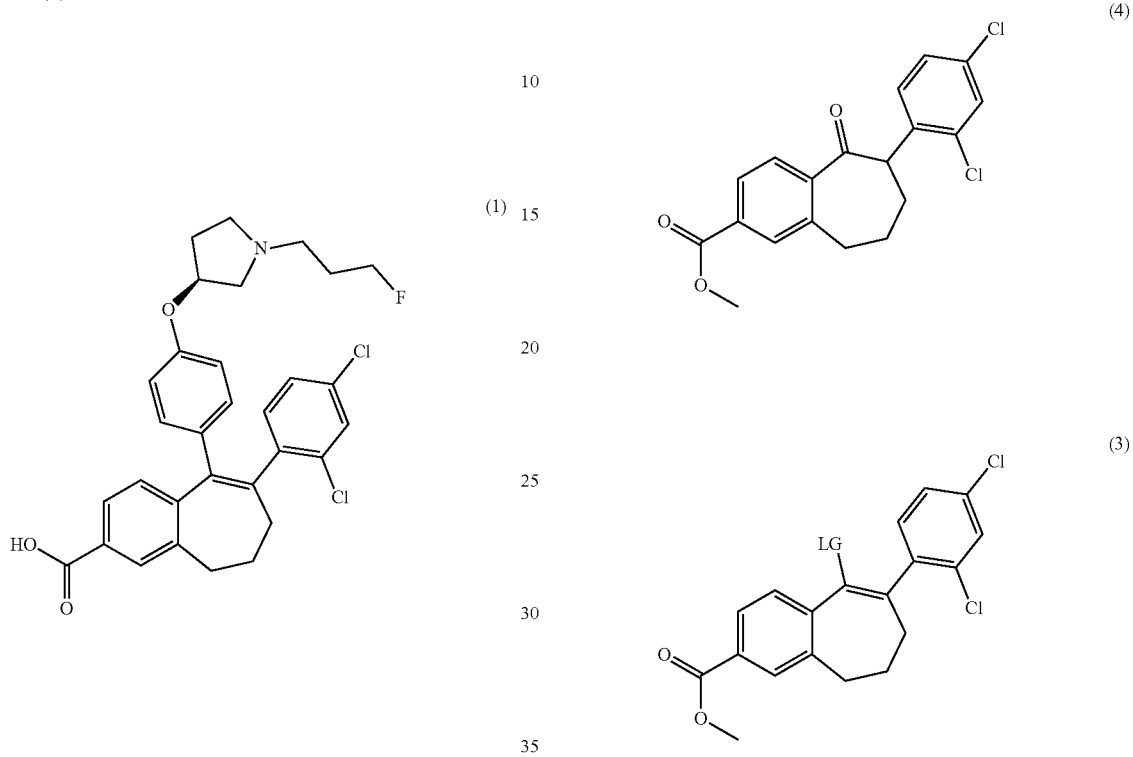

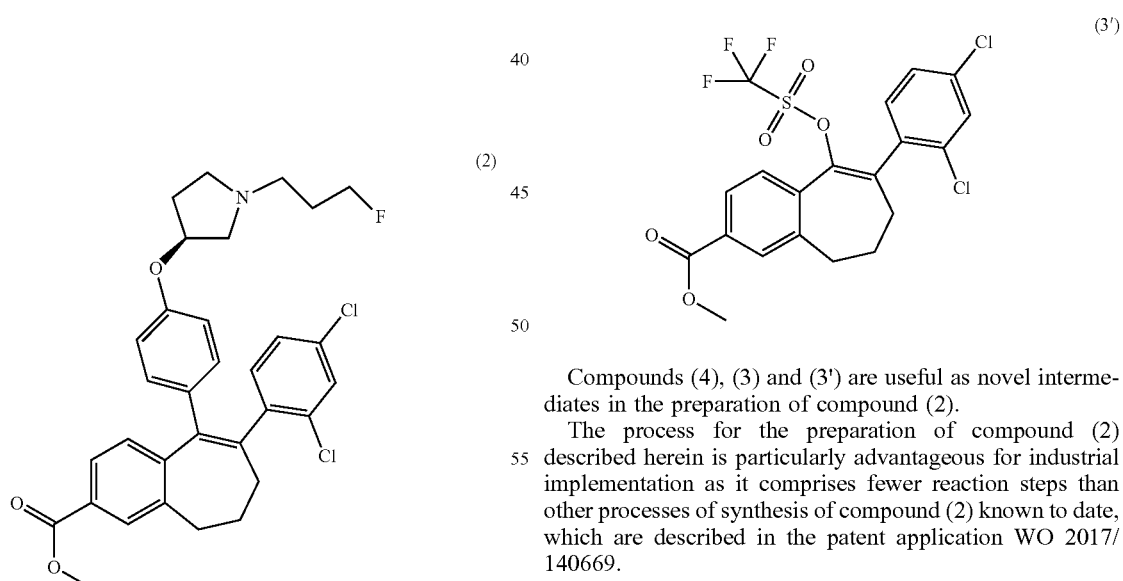

Compounds (4), (3) and (3') are useful as novel intermediates in the preparation of compound (2).

The process for the preparation of compound (2) described herein is particularly advantageous for industrial implementation as it comprises fewer reaction steps than other processes of synthesis of compound (2) known to date, which are described in the patent application WO 2017/140669.

Scheme 3 below illustrates the shortest process for the synthesis of compound (2) described in WO 2017/140669. In scheme 3, each intermediate is designated under the same name as provided in said international patent application. This process as illustrated in scheme 3, starting from the commercially available intermediate 2-methoxy-6,7,8,9-tetrahydro-5H-benzo[7]annulen-5-one, is hereafter designated as "route A".

Scheme 3: Route A

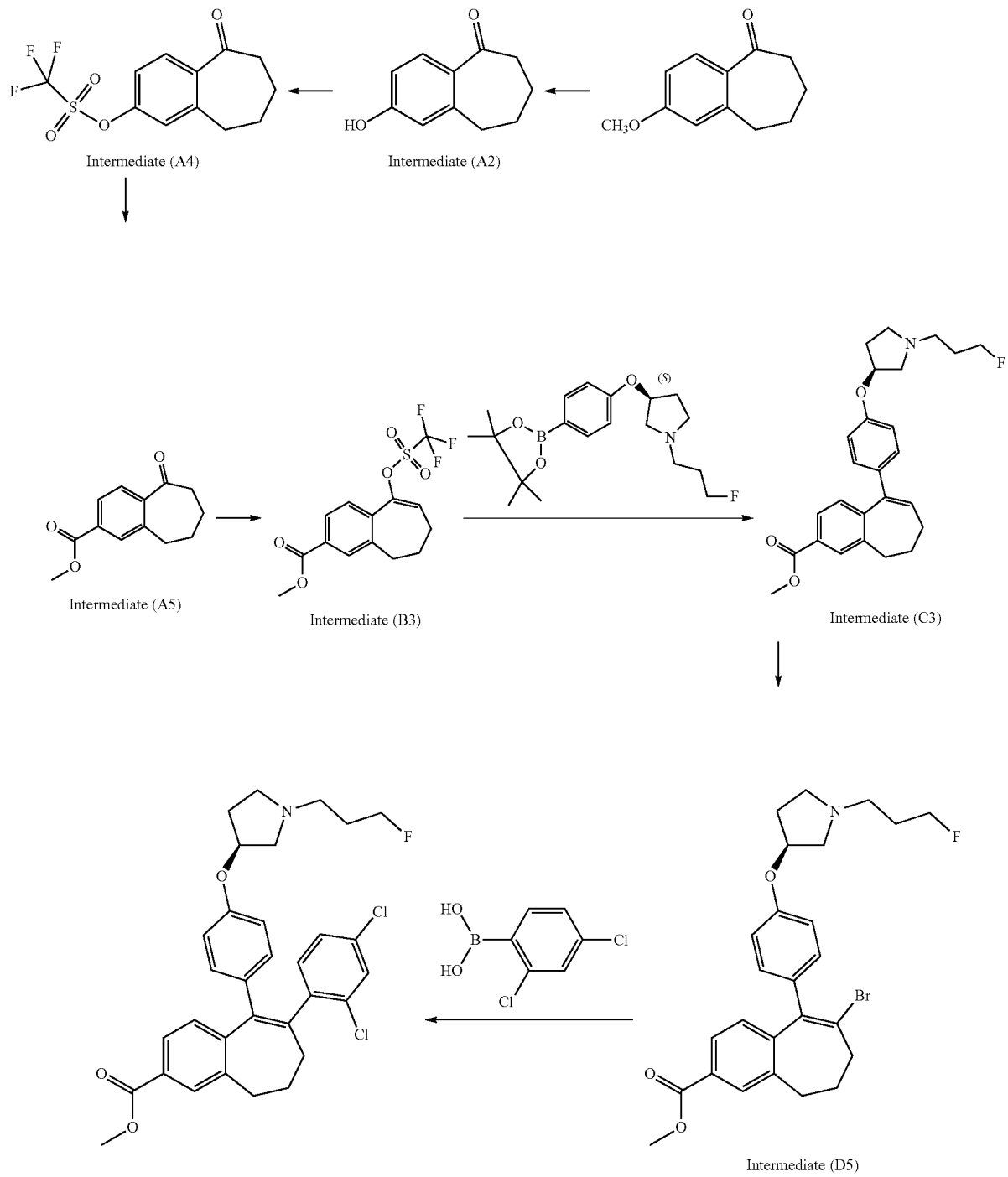

Under route A illustrated in scheme 3, compound (2) is obtained in 4 steps starting from methyl 5-oxo-6,7,8,9-tetrahydro-5H-benzo[7]annulene-2-carboxylate (same compound designated as "compound (5)" herein and as "intermediate (A5)" in WO 2017/140669). The process for the preparation of compound (2) described herein therefore allows to obtain this compound in only 3 steps starting from methyl 5-oxo-6,7,8,9-tetrahydro-5H-benzo[7]annulene-2-carboxylate, compared to route A.

A second process of synthesis of compound (2) is described in WO 2017/140669, starting from the same intermediates 2-methoxy-6,7,8,9-tetrahydro-5H-benzo[7]annulen-5-one and intermediate (A2) as in scheme 3 above. This second process of synthesis of compound (2) is illustrated in scheme 4 below, wherein each intermediate is designated under the same name as provided in patent application WO 2017/140669. This process under scheme 4 is hereafter designated as "route B".

Scheme 4: Route B
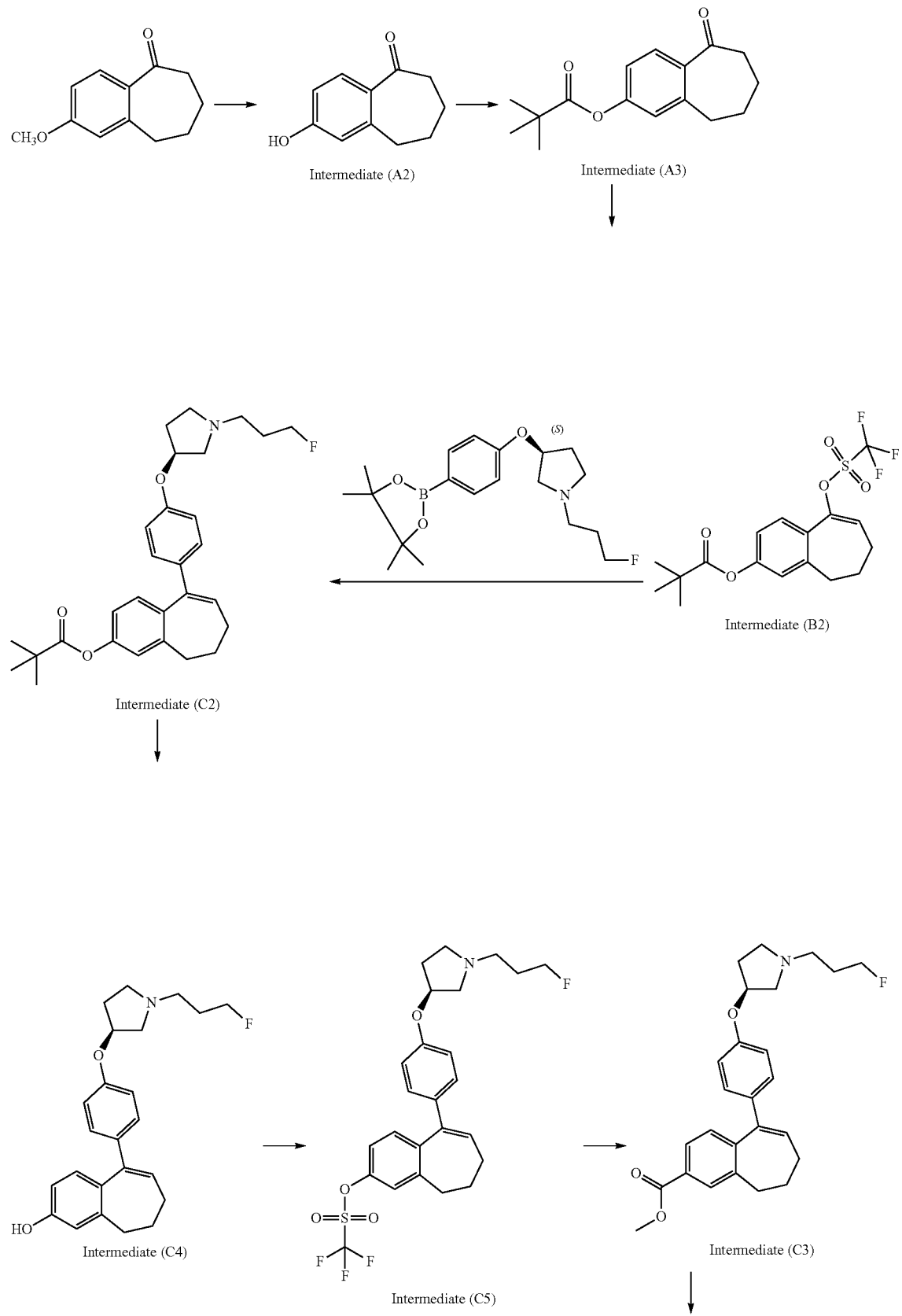

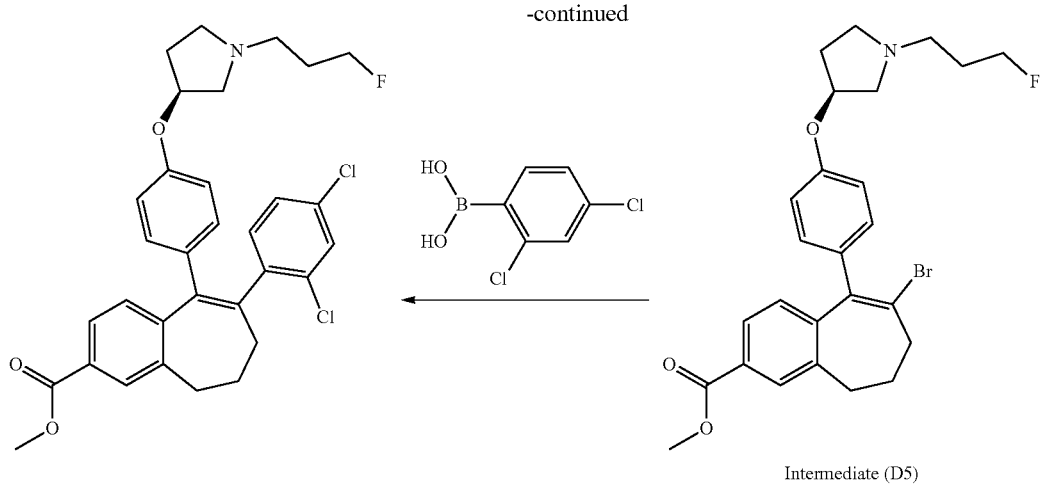

Intermediate (D5)

It therefore appears that the process for the preparation of compound (2) under scheme 4 entails many more reaction steps than the one under scheme 3.

Hence the process for the synthesis of compound (2) as described herein is shorter in terms of number of steps compared to both routes A and B as described in WO 2017/140669.

Below are described examples of protocols for the synthesis of salts of compound (2), according to the processes of synthesis described herein.

EXAMPLE 1

Preparation of the Organoboron Derivative "Reagent (1)"

The preparation of reagent (1), useful in the Suzuki coupling step of the process for synthesis of compound (2) as described herein, is illustrated in scheme 5 below, reproduced from the patent application WO 2017/140669.

SCHEME 5

STEP 1

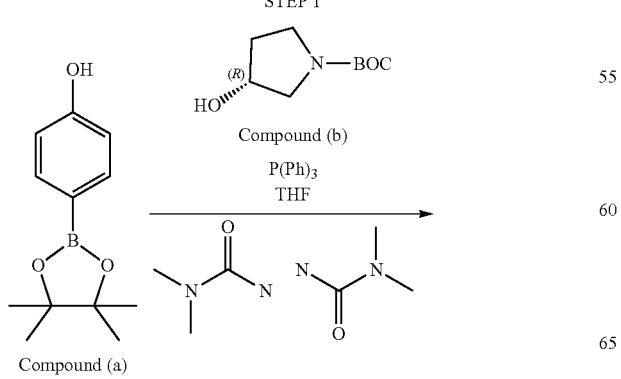

Compound (a)

Compound (b)

P(Ph)₃
THF

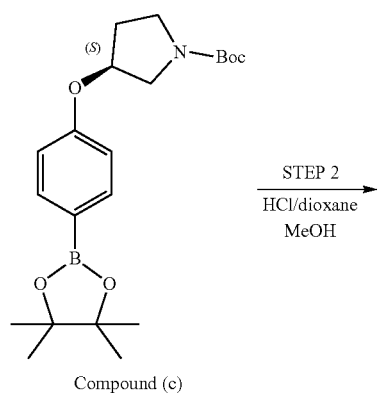

Compound (c)

STEP 2
HCl/dioxane
MeOH

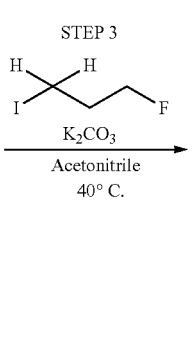

Compound (d)

STEP 3
K₂CO₃
Acetonitrile
40° C.

-continued

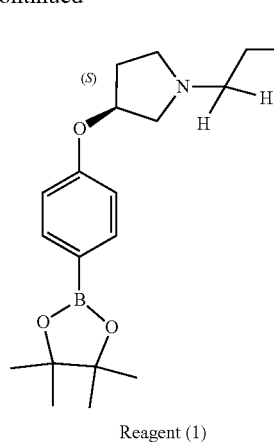

Reagent (1)

According to scheme 5, the commercially available compound (a) (4-(4,4,5,5-tetramethyl-1,3,2-dioxaborolan-2-yl) phenol) is condensed in tetrahydrofuran (THF) at room temperature on (R)-1-N-Boc-3-hydroxypyrrolidine, using N,N',N'-tetramethylazodicarboxamide as coupling agent.

According to step 2, the compound (c) thus obtained is N-deprotected in methanol (MeOH) at room temperature using an acidic agent, for example a solution of HCl 4N in dioxane.

Alkylation of the pyrrolidine nitrogen is then performed under step 3 by reacting compound (d) with the corresponding 1,1-disubstituted 1-halogeno-3-fluoro propane, for example 1-iodo-3-fluoropropane, in acetonitrile in presence of potassium carbonate ($K_2CO_3$) at about 40° C.

Steps 1 to 3 of scheme 5 are illustrated by the detailed protocols below.

The $^1$H NMR spectra were performed on a Bruker Avance DRX-400 spectrometer, with the chemical shifts (δ in ppm) in the solvent dimethyl sulfoxide-d6 (dDMSO-d6) referenced at 2.50 ppm at a temperature of 303 K. Coupling constants (J) are given in Hertz.

The liquid chromatography/mass spectrography (LC/MS) data were obtained on a UPLC Acquity Waters instrument, light scattering detector Sedere and SQD Waters mass spectrometer using UV detection DAD 210<1<400 nm and column Acquity UPLC CSH C18 1.7 μm, dimension 2.1×30 mm, mobile phase $H_2O$+0.1% $HCO_2H$/$CH_3CN$+0.1% $HCO_2H$.

Compound (c). Tert-butyl (3S)-3-[4-(4,4,5,5-tetramethyl-1,3,2-dioxaborolan-2yl)phenoxy]pyrrolidine-1-carboxylate

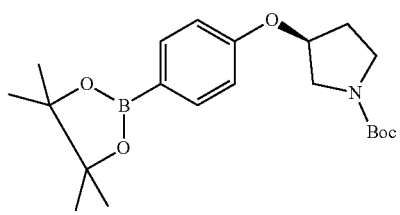 [SMILES: CC(C)(C)OC(=O)N1CC[C@H](Oc2ccc(B3OC(C)(C)C(C)(C)O3)cc2)C1]

To a solution of 4-(4,4,5,5-tetramethyl-1,3,2-dioxaborolan-2-yl)phenol (a) (82.7 g, 364.51 mmol) in THF (2 L) was added under argon (R)-1-N-Boc-3-hydroxypyrrolidine (b) (84.43 g, 437.41 mmol) followed by N,N,N',N'-tetramethylazodicarboxamide (99.1 g, 546.77 mmol). The clear reaction mixture turned orange and triphenylphosphine (143.41 g, 546.77 mmol) was added. The reaction mixture was stirred at room temperature for 24 hours, meanwhile a precipitate of triphenylphosphine oxide formed ($Ph_3P$=O). The reaction mixture was poured in water (1.5 L) and extracted with ethyl acetate (AcOEt) (3×1.5 L). Gathered organic phases were dried over magnesium sulfate ($MgSO_4$), filtered and concentrated under reduced pressure. The residue was taken up into diisopropylether (1.5 L) and the solid formed ($Ph_3P$=O) was filtered. The solvent was concentrated under reduced pressure and the residue purified by column chromatography eluting with a mixture of heptane with AcOEt (90/10; v/v) to give 145 g (100%) of tert-butyl (3S)-3-[4-(4,4,5,5-tetramethyl-1,3,2-dioxaborolan-2-yl)phenoxy]pyrrolidine-1-carboxylate (c) as a colorless oil.

$^1$H NMR (400 MHz, DMSO-d6, δ ppm): 1.27 (s, 12H); 1.39 (s, 9H); 2.05 (m, 1H); 2.14 (m, 1H); 3.37 (3H); 3.55 (m, 1H); 5.05 (s, 1H); 6.94 (d, J=8.4 Hz, 2H); 7.61 (d, J=8.4 Hz, 2H).

Compound (d). (3S)-3-[4-(4,4,5,5-tetramethyl-1,3,2-dioxaborolan-2yl)phenoxy]pyrrolidine, Hydrochloride

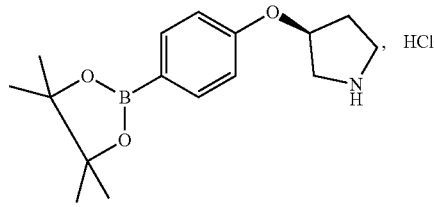 [SMILES: CC1(C)OB(c2ccc(O[C@H]3CCNC3)cc2)OC1(C)C ; Cl]

To a solution of (S)-tert-butyl 3-(4-(4,4,5,5-tetramethyl-1,3,2-dioxaborolan-2-yl)phenoxy)pyrrolidine-1-carboxylate (c) (80 g, 195.23 mmol) in MeOH (450 ml) was added slowly HCl 4N in dioxane (250 ml).

After 1.5 hours, the reaction mixture was concentrated under reduced pressure and the residue was taken up into $Et_2O$ with stirring to give a solid which then was filtered and dried under vacuum to give compound (d) 61.8 g (95%) as a white powder.

$^1$H NMR (400 MHz, DMSO-d6, δ ppm): 1.28 (s: 12H); 2.10 (m: 1H); 2.21 (m: 1H); 3.31 (3H); 3.48 (m: 1H); 5.19 (m: 1H); 6.97 (d, J=8.4 Hz: 2H); 7.63 (d, J=8.4 Hz: 2H); 9.48 (s: 1H); 9.71 (s: 1H).

LC/MS (m/z, MH$^+$): 290

Reagent (1). (3S)-1-(3-fluoropropyl)-3-[4-(4,4,5,5-tetramethyl-1,3,2-dioxaborolan-2-yl)phenoxy]pyrrolidine

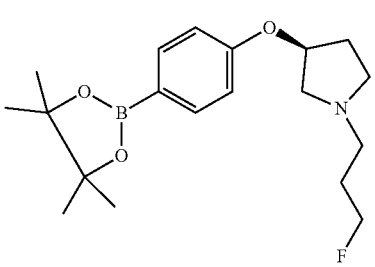 [SMILES: CC1(C)OB(c2ccc(O[C@H]3CCN(CCCF)C3)cc2)OC1(C)C]

To a suspension of (S)-3-(4-(4,4,5,5-tetramethyl-1,3,2-dioxaborolan-2-yl)phenoxy)pyrrolidine hydrochloride (d) (20 g, 61.42 mmol) in acetonitrile (100 ml), was added $K_2CO_3$ (21.22 g, 153.54 mmol) and 1-iodo-3-fluoropropane (12.15 g, 61.42 mmol), under argon. The reaction mixture was stirred at 40° C. for 24 hours. After cooling to room temperature, the reaction mixture was filtered and washed with acetonitrile. The filtrate was concentrated under reduced pressure and the residue was taken up in DCM and the solid formed was filtered and washed with DCM. The filtrate was concentrated to give reagent (1) 21.5 g (100%) as a yellow foam.

$^1$H NMR (400 MHz, DMSO-d6, δ ppm): 1.27 (s, 12H); 1.77 (m, 2H); 1.84 (m, 1H); 2.27 (m, 1H); 2.41 (m, 1H); 2.49 (2H); 2.62 (dd, J=2.6 and 10.4 Hz, 1H); 2.69 (m, 1H); 2.83 (dd, J=6.2 and 1.4 Hz, 1H); 4.47 (td, J=6.2 and 47 Hz, 2H); 4.99 (m, 1H); 6.77 (d, J=8.4 Hz, 2H); 7.58 (d, J=8.4 Hz, 2H).

LC/MS (m/z, MH$^+$): 350

EXAMPLE 2

Synthesis of Compound (2) from Carboxymethoxy-Benzosuberone (5)

The numbering of the intermediate and final compounds (2), (3'), (4) and (5) refer to scheme 2 described before.

In the first step S1, the 5-oxo-6,7,8,9-tetrahydrobenzo[7]annulene core of compound (5) (carboxymethoxybenzosuberone) is arylated at the 6-position via a palladium catalyzed coupling of 1-bromo-2,4-dichloro-benzene in refluxing toluene and in the presence of potassium carbonate, to yield the 2,4-dichlorophenyl precursor (4) isolated as a Me-THF solution after silica gel filtration.

In the second step S2, the crude Me-THF solution of compound (4) is reacted with N-phenyl-bis-triflimide in the presence of catalytic DBU and an excess of sodium hydride. After water washing and solvent exchange to acetonitrile, the desired triflated compound (3') is isolated by crystallization as a white solid.

In a third step S3, the cyclic enol triflate (3') is coupled to the chiral boronic ester "reagent (1)" as described earlier via a palladium catalyzed Suzuki reaction performed in an acetonitrile/water mixture at 40±3° C., using cesium carbonate as a base. After aqueous work-up and solvent exchange with isopropylacetate, residual palladium is eliminated by sequential ethylenediamine, charcoal and dimercaptotriazine grafted silica treatments. The crude oxalate salt of compound (2) is isolated by crystallization in isopropylacetate.

These steps are illustrated by the detailed protocols below.

The $^1$H NMR spectra were performed on a 300 or 400 MHz Bruker Avance spectrometer, with the chemical shifts (δ in ppm) in the solvent dimethyl sulfoxide-d6 (dDMSO-d6) referenced at 2.50 ppm at a temperature of 303 K. Coupling constants (J) are given in Hertz.

The liquid chromatography/mass spectrography (LC/MS) data were obtained on a UPLC-SQD Waters instrument, evaporating light scattering detector Sedere and SQD Waters mass spectrometer using UV detection DAD 210<l<400 nm and column Acquity UPLC CSH C18 1.7 μm, dimension 2.1×50 mm, mobile phase $H_2O$+0.1% $HCO_2H$/$CH_3CN$+0.1% $HCO_2H$.

2.1: Steps S1 and S2 Concatenated

A degassed mixture of methyl 5-oxo-6,7,8,9-tetrahydro-5H-benzo[7]annulene-2-carboxylate (5) (40 g), potassium carbonate ($K_2CO_3$, 40 to 101 g i.e. 1.5 to 4 eq.), bromo-dichlorobenzene (62.1 g), Xantphos (21.2 g) and $Pd_2dba_3$ (8.39 g) is refluxed in toluene (320 ml) under nitrogen and vigorous stirring until completion.

After cooling to room temperature, insoluble material is eliminated by filtration on a pad of silica (80 g), followed by washings of the filter with toluene (600 ml). Toluene is distilled off from the filtrate and exchanged with Me-THF to yield a solution of the α-arylation product (4) (methyl 6-(2,4-dichlorophenyl)-5-oxo-6,7,8,9-tetrahydrobenzo[7]annulene-2-carboxylate) in MeTHF (400 ml), used as is in the next step.

A sample of pure product (4) has been isolated by silica gel chromatography of an aliquot (eluent: dichloromethane-heptane).

$^1$H NMR (400 MHz, DMSO-d6 in ppm) of the isolated compound (4): 1.77 (m, 1H) 2.00 (m, 1H); 2.18 (m, 2H); 3.08 (m, 1H); 3.20 (m, 1H); 3.89 (s, 3H); 4.46 (dd, J=11.3, 3.7 Hz, 1H); 7.46 (m, 2H); 7.59 (d, J=2.0 Hz, 1H); 7.64 (d, J=7.9 Hz, 1H); 7.91 (dd, J=8.0, 1.4 Hz, 1H); 7.94 (s, 1H).

LC/MS ([M+H]$^+$): 363

To the Me-THF solution of compound (4) obtained in step S1 (scale: 40 g of compound (4)) is added N,N-bis(trifluoromethylsulfonyl)aniline (80 g). The resulting solution is added dropwise at 0° C., under stirring, to a Me-THF (200 ml) suspension of NaH (10 g—60% dispersion in oil) containing DBU (5 ml). The reaction mixture is stirred at room temperature until completion.

After cooling to 0° C., acetic acid (4 ml), followed by water (400 ml), are added dropwise. The aqueous phase is separated at room temperature and the organic phase is washed with diluted aqueous sodium chloride (NaCl, 0.6 M; 3×400 ml). Me-THF is distilled off and exchanged with acetonitrile. After elimination of insoluble material by filtration in hot acetonitrile, compound (3') (methyl 6-(2,4-dichlorophenyl)-5-(trifluoromethylsulfonyloxy)-8,9-dihydro-7H-benzo[7]annulene-2-carboxylate) is crystallized in 250 ml of acetonitrile, isolated by filtration and washings with cold acetonitrile and heptane, to yield 61.2 g of pure triflate as a white solid.

Yield: 67.4% (in 2 steps S1 and S2).

$^1$H NMR (400 MHz, DMSO-d6 in ppm): 2.18 (m, 2H); 2.41 (m, 2H); 2.95 (m, 2H); 3.90 (s, 3H); 7.55 (m, 2H); 7.68 (d, J=8 Hz, 1H); 7.80 (d, J=1.8 Hz, 1H) 8.01 (m, 2H).

LC/MS (EI m/z): 494$^+$

Purity of compound (3'): 99.0%, measured by HPLC:

Mobile phase: water/acetonitrile/HCOOH;

Stationary phase: XSelect CSH C18-3.5 μm (Waters) or equivalent;

Column length: 100 mm;

Column internal diameter: 4.6 mm;

Flow rate: 1 mL/minute;

Injection volume: 10 μL;

Detection: 254 nm (UV).

2.2: Step S3

A degassed mixture of the triflate (3') (20 g), the boronic ester "reagent (1)" (14.1 g), $Cs_2CO_3$ (19.7 g), bis(triphenylphosphine) palladium(II)dichloride (1.4 g), water (100 ml) and acetonitrile (260 ml), is stirred at 40° C. under nitrogen. After complete conversion, the reaction medium is cooled to room temperature, isopropylacetate (100 ml) is added and the aqueous phase is separated. The organic phase is washed with diluted aqueous NaCl (0.3 M; 2×200 ml), dried by azeotropic distillation of isopropylacetate and treated subsequently with ethylenediamine, charcoal and dimercaptotriazine grafted silica, to remove residual palladium.

The resulting solution of compound (2), namely 6-(2,4-dichlorophenyl)-5-{4-[1-(3-fluoro-propyl)-pyrrolidin-3-yloxy]-phenyl}-8,9-dihydro-7H-benzocycloheptene-2-carboxylic acid methyl ester, in isopropylacetate, adjusted at 200 ml, is heated to 70° C. and an oxalic acid (3.6 g) solution in isopropylacetate (43 ml) is added dropwise under stirring. After seeding (using seeds previously prepared on another batch of product by conventional crystallisation techniques) and cooling to 0° C., the desired oxalate salt of compound (2), depicted below, crystallizes and is isolated by filtration in a 70% yield (18.6 g, white powder):

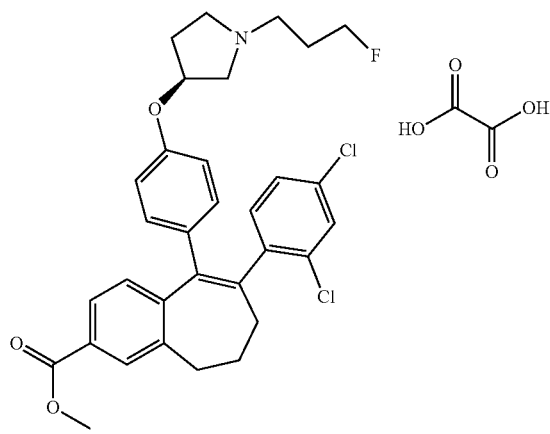 [SMILES: COC(=O)c1ccc2c(c1)CCCC(c1ccc(Cl)cc1Cl)=C2c1ccc(O[C@H]2CCN(CCCF)C2)cc1 ; O=C(O)C(=O)O]

$^1$H NMR (400 MHz, DMSO-d6 in ppm): 7.92 (d, J=2.0 Hz, 1H); 7.78 (dd, J=8.0 and 2.0 Hz, 1H); 7.59 (d, J=2.2 Hz, 1H); 7.29 (dd, J=8.3 and 2.2 Hz, 1H); 7.22 (d, J=8.3 Hz, 1H); 6.90 (d, J=8.0 Hz, 1H); 6.78 (d, J=9.0 Hz, 2H); 6.73 (d, J=9.0 Hz, 2H); 4.98 (m, 1H); 4.50 (dt, J=47.2 and 5.7 Hz, 2H); 3.86 (s, 3H); 3.49 (dd, J=12.8 and 5.8 Hz, 1H); from 3.38 to 3.08 (m, 5H); 2.94 (t, J=5.0 Hz, 2H); 2.34 (m, 1H); from 2.23 to 2.11 (m, 3H); from 2.07 to 1.93 (m, 2H).

LC/MS ([M+H]$^+$): 568

Purity of compound (2), oxalate salt: 98.2%, measured by HPLC under the same conditions as described in step S2 above.

EXAMPLE 3

Alternative Protocols for Step S1

3.1: Alternative 1

A 2 M THF solution of sodium tert-butoxide (19.48 ml) is added dropwise at 60° C. to a degassed mixture containing compound (5) (5 g), 1-bromo-2,4-dichlorobenzene (7.76 g), palladium acetate (257 mg), Xantphos (660 mg) and THF (20 ml). The reaction is heated at 60° C. until completion, cooled to room temperature, quenched with molar aqueous KH$_2$PO$_4$. After ethyl acetate extraction, water washings and purification by silica gel chromatography, compound (4) is isolated in a 70% yield and 92% purity.

$^1$H NMR (400 MHz, DMSO-d6 in ppm): 1.78 (m, 1H); 2.01 (m, 1H); 2.19 (m, 2H); 3.10 (m, 1H); 3.22 (m, 1H); 3.89 (s, 3H); 4.47 (dd, J=11.3, 3.6 Hz, 1H); 7.47 (m, 2H); 7.61 (d, J=1.8 Hz, 1H); 7.92 (d, J=7.9 Hz, 1H); 7.92 (d, J=7.7 Hz, 1H); 7.95 (s, 1H).

LC/MS ([M+H]$^+$): 363

3.2: Alternative 2

A degassed mixture containing compound (5) (0.5 g), 1-iodo-2,4-dichlorobenzene (0.76 ml), toluene (9 ml), water (1 ml), Cs$_2$CO$_3$ (1.05 g), palladium acetate (50 mg) and Xantphos (250 mg) is heated to reflux during about 22 hours. After cooling to room temperature, the organic phase is diluted with dichloromethane, washed with water and purified by chromatography on silica gel to yield 730 mg (87%) of a white solid.

$^1$H NMR (400 MHz, DMSO-d6 in ppm): 1.78 (m, 1H); 2.01 (m, 1H); 2.19 (m, 2H); 3.09 (m, 1H); 3.21 (m, 1H); 3.89 (s, 3H); 4.47 (dd, J=11.3, 3.7 Hz, 1H); 7.47 (m, 2H); 7.60 (d, J=2.0 Hz, 1H); 7.64 (d, J=8.1 Hz, 1H); 7.92 (dd, J=7.9, 1.5 Hz, 1H); 7.95 (s, 1H).

EXAMPLE 4

Alternative Protocols for Step S2

3.1: Alternative 1

A 0.5 M THF solution of potassium bis-trimethylsilylamide (7.70 ml) is added dropwise at −50° C. to a mixture of compound (4) (1 g) and N-phenylbis-triflimide (1.22 g) in THF (18 ml). After warming up to room temperature, the reaction medium is quenched with water at 0-5° C., extracted with dichloromethane followed by ethyl acetate, and purified by silica gel chromatography (eluent: dichloromethane-heptane) to afford the desired compound (3') in an 80% yield and 90% purity measured by LC/MS.

$^1$H NMR (400 MHz, DMSO-d6 in ppm): 2.18 (m, 2H); 2.41 (m, 2H); 2.95 (m, 2H); 3.89 (s, 3H); 7.55 (m, 2H); 7.68 (d, J=8.1 Hz, 1H); 7.80 (d, J=1.7 Hz, 1H); 8.01 (m, 2H).

LC/MS ([M+H]$^+$): 494

3.2: Alternative 2

DBU (247 µl) is added dropwise at 0-5° C. to a suspension containing compound (4) (500 mg), and N,N-bis(trifluoromethylsulfonyl)aniline (639 mg) in acetonitrile (2 ml). The conversion rate is about 80% after stirring 22 hours at room temperature. The reaction mixture is cooled down to 0-5° C. and sodium hydride (27.5 mg of a 60% dispersion in oil) is added. After 1.5 hours stirring at room temperature, the conversion rate is about 100%. The resulting suspension is cooled down to 0-5° C., filtrated and washed with pre-cooled acetonitrile (0.5 ml) followed by water (2 ml) to yield 460 mg of compound (3') as a white powder (yield: 67.5%) with a purity of 98% measured by LC/MS.

$^1$H NMR (400 MHz, DMSO-d6 in ppm): 2.18 (m, 2H); 2.42 (m, 2H); 2.95 (m, 2H); 3.90 (s, 3H); 7.55 (m, 2H); 7.68 (d, J=7.9 Hz, 1H); 7.82 (s, 1H); 8.02 (m, 2H).

As shown in the above examples, the process of synthesis for salts of compound (2) described herein allows a global yield, from compound (5) to compound (2), of about 33 to 49%. This is a greater yield than the one found in the previously described process of synthesis as set forth in scheme 3, wherein the yield for obtaining compound (2) is about 26% when starting from the same compound methyl 5-oxo-6,7,8,9-tetrahydro-5H-benzo[7]annulene-2-carboxylate.

Also, the process of synthesis described herein allows to obtain compound (2) in novel salt forms in a good yield without the need to perform column chromatographies after the Suzuki coupling step, which was needed in the syntheses routes previously known involving base form of compound (2), but which is not appropriate when seeking a synthesis route applicable at the industrial level.

EXAMPLE 5

Synthesis of Compound (2) in the Form of a Dibenzoyl Tartrate Salt

A degassed mixture of methyl 8-bromo-9-(4-{[(3S)-1-(3-fluoropropyl)pyrrolidin-3-yl]oxy}phenyl)-6,7-dihydro-5H-benzo[7]annulene-3-carboxylate hydrobromide (25.0 g), 2,4-dichlorophenylboronic acid (9.9 g), $K_2CO_3$ (11.9 g), bis(triphenylphosphine) palladium(II)dichloride (1.4 g), water (75 ml) and 1,4-dioxane (206 ml), is stirred at 60° C. under nitrogen. Then 2,4-dichlorophenylboronic acid (9.9 g) is solubilized in a mixture of water and 1,4-dioxane (25 ml) and added. After complete conversion, the reaction medium is cooled to room temperature, and pyrrolidinedithiocarbamate (1.4 g) in water (50 ml) is added. The mixture is stirred at 20° C. and filtered. The filter is washed with toluene and the aqueous phase is separated. The organic phase is washed with diluted aqueous NaCl (2 M, 3×75 ml). Then charcoal (2.5 g) and $Al_2O_3$ (50.1 g) are added at 20° C. The mixture is filtered and the filter is washed with toluene (3×50 ml). The organic phase is concentrated to 1.8 volumes in order to remove a part of 1,4-dioxane.

(−)dibenzoyltartaric acid (15.4 g) is added to the resulting solution of compound (2), namely 6-(2,4-dichlorophenyl)-5-{4-[1-(3-fluoro-propyl)-pyrrolidin-3-yloxy]-phenyl}-8,9-dihydro-7H-benzocycloheptene-2-carboxylic acid methyl ester. N-heptane (300 ml) is added dropwise under stirring at 20° C. The dibenzoyltartaric salt of compound (2) is isolated by filtration in a 85% yield (43.3 g).

RMN $^1$H (400 MHz, DMSO-$d_6$ in ppm): 1.82-1.98 (m, 3H); 2.09-2.30 (m, 5H); 2.89-3.22 (m, 7H); 3.39 (m, 1H); 3.86 (s, 3H); 4.39 (td, J=5.9 and 47.4 Hz, 2H); 4.87 (m, 1H); 5.76 (s, 2H); 6.67 (d, J=8.9 Hz, 2H); 6.75 (d, J=8.9 Hz, 2H); 6.90 (d, J=8.1 Hz, 1H); 7.20 (d, J=8.4 Hz, 1H); 7.29 (dd, J=2.0 and 8.4 Hz, 1H); 7.54 (t, J=7.9 Hz, 4H); 7.60 (d, J=2.0 Hz, 1H); 7.68 (tt, J=1.3 and 7.9 Hz, 2H); 7.79 (dd, J=1.8 and 8.1 Hz, 1H); 7.96 (d, J=1.8 Hz, 1H); 7.98 (t, J=7.9 Hz, 4H); 10.70 (m spread, 1H); 13.00 (m spread, 1H).

The liquid chromatography/mass spectrography (LC/MS) data were obtained as follows:

Analytical Data in Mass Spectrometry
M$^+$=568 g·mol−1
M' (salt)=358 g·mol−1
Mass spectrometer: Waters UPLC-SQD, electrospray ionization (ES+/−)
Chromatographic conditions:
Column: ACQUITY UPLC CSH C18-1.7 µm-2.1×50 mm
Solvents: A: $H_2O$ (+0.1% formic acid) B: CH3CN (+0.1% formic acid)
Column temperature: 45° C.
Rate: 0.85 ml/min
Gradient (2.5 min): from 5 to 100% of B in 2.5 min; 2.40 min 100% B; from 100 to 5% of B in 0.05 min
UV: from 190 to 380 nm
Results:
at 1.12 min (31% in UV purity): m/z=357 in ES− corresponding to [M'−H]$^−$
at 1.17 min (67% in UV purity): m/z=568 in ES+ corresponding to [M]$^+$ Purity of Compound (2), Dibenzoyltartaric Salt: 93.2%, Measured by HPLC.

EXAMPLE 6

Salification Studies for Compound (2)

The oxalate and dibenzoyl tartrate salts of compound (2) are particularly advantageous in that they precipitate and crystalize from the reaction medium, allowing to recover salts of compound (2) from the reaction medium. The base form of compound (2) did not allow to isolate the product from the reaction medium, whatever the solvents and temperatures tested. Amongst a variety of salts tested with compound (2), the oxalate and dibenzoyl tartrate salts were the only ones to allow a frank precipitation, as shown in table 1 below.

TABLE 1 salification studies for compound (2) used at a scale of 0.25 g of the base form and at a temperature of 20° C.

| Solvent (5 volumes) | Acid (1 eq.) | Visual observations |
| --- | --- | --- |
| Toluene | Dibenzoyl tartaric acid | Precipitates with heptane |
| MIBK (methyl-isobutyl-ketone) | Dibenzoyl tartaric acid | No precipitation |
| MTBE (methyl-tertbutyl-ether) | Dibenzoyl tartaric acid | No precipitation |
| Heptane | Dibenzoyl tartaric acid | No precipitation |
| Ethyl acetate | Dibenzoyl tartaric acid | No precipitation |
| Ethyl acetate | Sulfuric acid | No precipitation |
| Toluene | Sulfuric acid | No precipitation |
| Ethyl acetate | Glyoxylic acid | No precipitation |
| Toluene | Glyoxylic acid | Slight precipitation |
| Ethyl acetate | Trifluoromethanesulfonic acid | No precipitation |
| Toluene | Trifluoromethanesulfonic acid | No precipitation |
| Ethyl acetate | Formic acid | Slight precipitation |
| Toluene | Formic acid | Precipitation, followed by gum formation |
| Ethyl acetate | Trifluoroacetic acid | Slight precipitation |
| Toluene | Trifluoroacetic acid | No precipitation |
| Ethyl acetate | Phosphomolybdic acid | No precipitation |
| Toluene | Phosphomolybdic acid | No precipitation |
| Ethyl acetate | Lactic acid | No precipitation |
| Toluene | Lactic acid | Slight precipitation |
| Ethyl acetate | Isethionic acid (0.5N in water) | Slight precipitation |
| Toluene | Isethionic acid (0.5N in water) | Slight precipitation |
| Toluene | Succinic acid | No precipitation |
| Toluene | Citric acid | No precipitation |
| Toluene | Fumaric acid | Slight precipitation |
| Toluene | Stearic acid | Slight precipitation |
| Toluene | Oxalic acid | Precipitates |
| MIBK | Oxalic acid | No precipitation |
| MTBE | Oxalic acid | Precipitates |
| Acetonitrile | Oxalic acid | No precipitation |
| Ethanol | Oxalic acid | No precipitation |
| Ethyl acetate | Oxalic acid | Precipitates |
| Isopropyl alcohol | Tartaric acid | No precipitation |
| MIBK | Tartaric acid | Precipitates, but few product, which is hygroscopic |
| Acetonitrile | Tartaric acid | No precipitation |
| MIBK | Methanesulfonic acid | No precipitation |
| Toluene | Naphtalene-sulfonic acid | No precipitation |
| MIBK | Naphtalene-sulfonic acid | No precipitation |
| MTBE | Naphtalene-sulfonic acid | No precipitation |
| Ethyl acetate | Naphtalene-sulfonic acid | No precipitation |
| Heptane | Naphtalene-sulfonic acid | No precipitation |
| Toluene | Naphtalene-disulfonic acid | No precipitation |

TABLE 1-continued salification studies for compound (2) used at a scale of 0.25 g of the base form and at a temperature of 20° C.

| Solvent (5 volumes) | Acid (1 eq.) | Visual observations |
| --- | --- | --- |
| MIBK | Naphtalene-disulfonic acid | No precipitation |
| MTBE | Naphtalene-disulfonic acid | No precipitation |
| Ethyl acetate | Naphtalene-disulfonic acid | No precipitation |
| Heptane | Naphtalene-disulfonic acid | No precipitation |

The invention claimed is:

1. An oxalate salt of 6-(2,4-dichlorophenyl)-5-{4-[1-(3-fluoro-propyl)-pyrrolidin-3-yloxy]-phenyl}-8,9-dihydro-7H-benzocycloheptene-2-carboxylic acid methyl ester of the formula below:

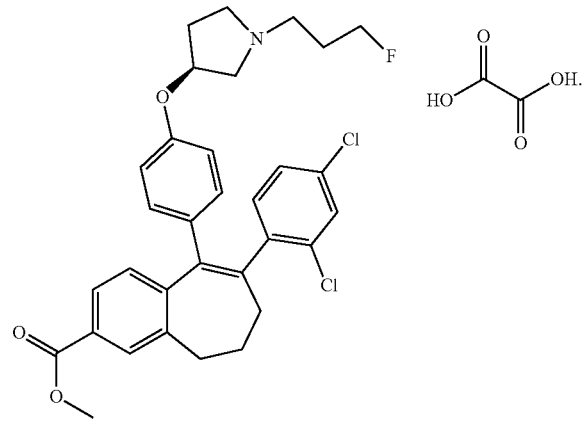 [SMILES: COC(=O)c1ccc2c(c1)CCCC(c1ccc(Cl)cc1Cl)=C2c1ccc(O[C@H]2CCN(CCCF)C2)cc1 ; O=C(O)C(=O)O]

2. A dibenzoyl tartaric salt of 6-(2,4-dichlorophenyl)-5-{4-[1-(3-fluoro-propyl)-pyrrolidin-3-yloxy]-phenyl}-8,9-dihydro-7H-benzocycloheptene-2-carboxylic acid methyl ester of the formula below:

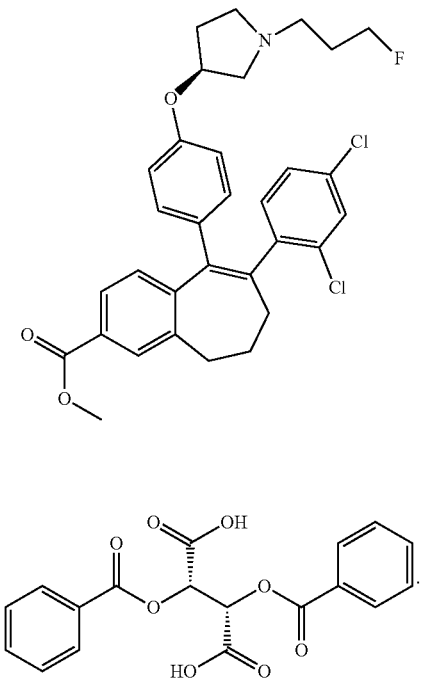

* * * * *